US005633359A

United States Patent [19]
Beaulieu

[11] Patent Number: 5,633,359
[45] Date of Patent: May 27, 1997

[54] METHOD FOR MAKING ALKYL POLYGLYCOSIDES

[75] Inventor: James D. Beaulieu, West Chester, Ohio

[73] Assignee: Henkel Corporation, Plymouth Meeting, Pa.

[21] Appl. No.: 502,878

[22] Filed: Jul. 17, 1995

Related U.S. Application Data

[63] Continuation of Ser. No. 179,453, Jan. 10, 1994, abandoned.

[51] Int. Cl.$^6$ ............................. C07G 3/00; C07H 1/00; C07H 15/04
[52] U.S. Cl. ................ 536/18.6; 536/18.5; 536/124
[58] Field of Search .................... 536/18.5, 18.6, 536/124

[56] References Cited

U.S. PATENT DOCUMENTS 4,987,225  1/1991  Pickens et al. ................... 536/18.6
5,079,350  1/1992  Fujita et al. ..................... 536/18.6

OTHER PUBLICATIONS

Chemical Engineering, issued Sep. 13, 1965, R. Fischer, "Part 3: Process Applications", pp. 186–190.

Primary Examiner—John Kight
Assistant Examiner—Everett White
Attorney, Agent, or Firm—Wayne C. Jaeschke; John E. Drach; Henry E. Millson, Jr.

[57] ABSTRACT

Alkyl polyglycoside products having improved color properties are produced by a process which involves reacting a reducing sugar with an alcohol to obtain an alkyl polyglycoside reaction product containing unreacted alcohol which is removed in a thin film evaporator wherein the alkyl polyglycoside product film is contacted by liquid water which cools the film and reduces the amount of color bodies in the product.

9 Claims, No Drawings

METHOD FOR MAKING ALKYL POLYGLYCOSIDES

This application is a continuation, of application Ser. No. 08/179,453 filed Jan. 10, 1994, now abandoned.

BACKGROUND OF THE INVENTION

1. Field of the Invention

This invention relates to a process for the production of an alkyl polyglycoside. More specifically, the present invention relates to a process for the production of an alkyl polyglycoside having improved color properties.

2. Description of the Related Art

Alkyl polyglycosides are glucose ethers wherein the anomeric alcohol group is replaced by an alkoxy group. Some of the glucose moieties are oligomerized such that a typical alkyl polyglycoside sample is comprised of a mixture of isomeric monoglycosides, diglycosides, triglycosides, etc., with each higher oligomer present in decreasing amounts. Alkyl polyglycosides have an average degree of oligomerization (DP) of from 1.4 to 1.7 units of glucose. Alkyl polyglycosides are conveniently prepared by reacting an alcohol of the type and chain length which is desired to form the "alkyl" portion of the glycoside of interest with a saccharide reactant (e.g., a monosaccharide such as glucose, xylose, arabinose, galactose, fructose, etc., or a polysaccharide such as starch, hemicellulose, lactose, maltose, melibiose, etc.) or with a glycoside starting material wherein the aglycone portion thereof is different from the alkyl substituent desired for the ultimate alkyl glycoside product of interest. Typically, such reaction is carried out under conditions wherein the alcohol is present in a mole ratio of alcohol/glucose in the range of from 2.0 to 5.0, at an elevated temperature and in the presence of an acid catalyst. The product contains alkyl polyglycoside and excess alcohol which is normally removed by distilling the alcohol from the alkyl polyglycoside product. Because the alcohol distillation operation requires temperatures in excess of 150° C., thermal degradation of the alkyl polyglycoside normally takes place and produces an undesirable color in the product. The alcohol-free alkyl polyglycoside product is then normally subjected to one or more decolorization operations wherein the product is reacted with hydrogen peroxide or a Group I or Group II metal borohydride to remove any color bodies which may have been formed during the prior process steps such as the alcohol removal operation.

The shorter the time period that the alkyl polyglycoside product is exposed to the elevated temperatures required for efficient alcohol removal the less pronounced is the color development and the simpler the subsequent decolorization process becomes.

SUMMARY OF THE INVENTION

It has been discovered that alkyl polyglycoside products having improved color properties can be produced by a process which involves first reacting a sugar with alcohol to obtain an alkyl polyglycoside reaction product containing unreacted alcohol. The alkyl polyglycoside product containing the excess alcohol is then introduced into the input of a thin film evaporator, also known as a wiped film evaporator. The pressure inside the thin film evaporator is less than about 20 mm Hg and the temperature is in the range of from about 320° F. to about 410° F. Liquid water is injected at the end nearest the discharge of the thin film evaporator so that the water contacts the hot film of alkyl polyglycoside immediately before the film exits the thin film evaporator through the discharge opening. As a result, the water undergoes an almost instantaneous phase change to steam as a result of the contact with the hot film and the low absolute pressure. The heat necessary to vaporize the water is transferred from the hot alkyl polyglycoside film to the water thereby cooling the film and reducing its temperature by about 20° F.–50° F., depending upon the input rate of the injected water. The steam then counter-currently contacts the remaining portion of the hot alkyl polyglycoside film thereby increasing the efficiency of the alcohol removal by lowering the partial pressure of the alcohol. The injection of liquid water into or near the discharge of the thin film evaporator allows the evaporator to be operated at a lower temperature and the liquid alkyl polyglycoside exiting from the discharge has a lower temperature thereby reducing the tendency of the product alkyl polyglycoside to develop color. Additionally, the alkyl polyglycoside product has a higher viscosity which allows downstream pumping equipment to operate more efficiently.

DESCRIPTION OF THE PREFERRED EMBODIMENTS

Other than in the operating examples, or where otherwise indicated, all numbers expressing quantities of ingredients or reaction conditions used herein are to be understood as modified in all instances by the term "about".

The process according to the invention can be used in the production of an alkyl polyglycoside of the formula I:

$$RO(G)_n \qquad (I)$$

wherein R is a monovalent organic radical containing from about one to about 30 carbon atoms. Examples of such monovalent saturated aliphatic, unsaturated aliphatic or aromatic radicals include but are not limited to alkyl, hydroxyalkyl, alkenyl, hydroxyalkenyl, aryl, alkylaryl, hydroxyalkylaryl, arylalkyl, alkenylaryl, arylalkenyl, and the like. The preferred values of R are monovalent, saturated aliphatic groups which contain from 1 to about 18 carbon atoms and more preferably from 10 to about 18 carbon atoms. G represents a moiety derived from a reducing saccharide containing 5 or 6 carbon atoms and n is a number having an average value from 1 to about 6 and preferably from 1 to about 3 and most preferably from 1 to about 2. The preferred reducing saccharides are arabinose, xylose, glucose, galactose and combinations thereof.

The process according to the invention can be used in the production of derivatives of compounds of the formula I above including, for example, those in which one or more of the normally free (i.e., unreacted) hydroxyl groups of the saccharide moiety, G, have been alkoxylated, preferably, ethoxylated or propoxylated, so as to attach one or more pendant alkoxy or polyalkoxy groups in place thereof. In the case of the indicated alkoxylated derivatives, the amount of alkylene oxide, e.g., ethylene oxide, propylene oxide, employed will generally correspond to from about 1 to about 20 and preferably from about 3 to about 10 moles thereof per mole of saccharide moiety. Such derivatives have the formula II $$RO(R'O)_y(G)_n \qquad (II)$$

wherein R, G, and n are the same as those of formula I and wherein R' is a divalent hydrocarbon radical containing from 2 to about 4 carbon atoms and y is a number having an average value of from 1 to about 12.

Most preferably, the process according to the invention is best suited to the production of an alkyl polyglycoside of the formula I as defined above and in particular wherein the reducing saccharide is glucose and the product produced is an alkyl polyglucoside. The process according to the invention begins with the reaction of a fatty alcohol and a reducing saccharide such as glucose in the presence of an acid catalyst such as sulfuric acid, para toluenesulfonic acid, or mono- or polyalkylated aryl mono- or polysulfonic acids such as dodecylbenzenesulfonic acid. The reducing saccharide and the fatty alcohol are reacted at a temperature in the range of from about 200° F. to about 220° F. and at a pressure of from about 15 mm Hg to about 25 mm Hg while continuously removing the water formed during the reaction. After the reducing saccharide has been substantially all reacted with the alcohols, the acid catalyst is neutralized. The excess fatty alcohol is removed from the alkyl polyglycoside because the presence of higher alcohols are known to reduce the surfactant activity of the composition and to impact the odor of the product. Generally, the amount of alcohol remaining in the product is generally less than about 5% by weight of the product and preferably less than about 2% by weight and most preferably less than about 1.0% by weight of the product. The fatty alcohol removal is most efficiently accomplished in a two stage process. The first stage utilizes a forced circulation evaporation zone or falling film evaporation zone to remove a substantial portion of the unreacted fatty alcohol. The second stage involves passing the alkyl polyglycoside product with a reduced content of unreacted fatty alcohol to a wiped film evaporation zone to reduce the content of free fatty alcohol in the alkyl polyglycoside product to less than about 5% by weight, preferably less than about 2% by weight, and most preferably less than about 1.0% by weight of the mixture of fatty alcohol and alkyl polyglycoside product.

In the forced circulation evaporation zone, a reservoir of the reaction mixture having a portion of the fatty alcohol removed is maintained under a reduced pressure and at an elevated temperature. The pressure is generally in the range of from about 1.0 mm Hg to about 100 mmHg and a temperature in the range of from about 250° F. to about 350° F. The product is pumped through a heat exchange means at a rate to maintain a velocity of from about 2 to about 25 feet per second in the heat exchanger and then introduced into the forced circulation evaporating zone vessel above a reservoir of the fatty glycoside with the reduced fatty alcohol content. The stream of material which has passed through the heat exchange means can be sprayed over the top of the reservoir or introduced tangentially at points along the sides of the vessel containing the reservoir of fatty glycoside product with the reduced content of fatty alcohol.

The temperature of the heating material for the heat exchange means is generally maintained as close as possible to the required temperature of the circulating liquid stream. Preferably, the differential temperature between the heating material and the circulating liquid is in the range of less than about 100° F.–105° F., preferably less than about 85° F. and most preferably less than about 70° F. The liquid passing through the heat exchange means is maintained at a relatively high velocity to improve the heat transfer rate and reduce the difference in the temperature between the heating material and the circulating liquid to as low a value as practical. A restriction means such as a valve or an orifice is generally provided in the circulating system downstream of the heat exchange means to prevent boiling of the circulating liquid in the heat exchange means.

The neutralized reaction product which is introduced into the forced circulation evaporating zone can be introduced into the body of the liquid in the reservoir in the forced circulating evaporating vessel introduced into the suction or the discharge of the circulating pump so that the material is rapidly heated along with the circulating stream of the fatty glycoside product with the reduced fatty alcohol content.

The forced circulation evaporating zone can have mist elimination means to remove any materials which may tend to leave the forced circulation evaporation zone with the fatty alcohol vapors which are being separated from the fatty glycoside product. In addition, a stream of inert gas can be introduced into the reservoir of fatty glycoside product or into the vapor space above the reservoir of the fatty glycoside product to assist in reducing the content of fatty alcohol in the mixture. The forced circulating evaporating zone can be operated on a batch or a continuous basis. That is, the neutralized reaction product is introduced into the forced circulation evaporating zone and the reservoir of material circulated through the heat exchange means and returned to the reservoir of material in the forced circulating evaporating vessel until a composition with the desired content of fatty alcohol has been provided. At this point, a stream of the reaction product with reduced alcohol content is continuously introduced into the wiped film evaporation zone.

Preferably, the forced circulation evaporating zone is operated continuously wherein a stream of the neutralized reaction product is introduced continuously into the forced circulation evaporation zone and a stream of the forced evaporation zone product is introduced continuously into the wiped film evaporation zone.

Wiped film or thin film evaporators are well known in the art of separating high boiling point materials from heat sensitive products. In the wiped film evaporating zone, the feed comprising fatty alcohol and fatty glycoside product is introduced into the input of the zone along the peripheral surface of the evaporator and a series of wiper blades rotating in the wiped film evaporation zone continuously wipe and spread the mixture over the heated surfaces of the wiped film evaporating zone. The heated surfaces of the wiped film evaporation zone can be heated by well known means such as hot oil, steam or even electrically as the case may require. The wiped film is continuously moved toward the discharge end of the wiped film evaporator by means of gravity if the evaporator is oriented vertically or by a pumping means if the evaporator is oriented horizontally.

The wiped film evaporation zone is generally operated at a temperature and pressure to provide a product with the required fatty alcohol content. The temperature and pressure required in the wiped film evaporation zone is dependent upon the fatty alcohol which must be removed and the level of fatty alcohol permitted in the fatty glycoside product. Generally, the wiped film evaporator is operated at a pressure in the range of from about 0.1 mm to about 70 mm Hg, preferably less than 20 mm Hg and a product temperature in the range of from about 300° F. to about 450° F.

In the process according to the invention, liquid water is introduced at or, preferably, immediately before the discharge end of the wiped film evaporator so that the water contacts the portion of the alkyl polyglycoside product film closest to the discharge of the evaporator. The water that contacts the hot film of alkyl polyglycoside rapidly undergoes a phase change to steam as a result of the contact with the hot film under the low pressure conditions. The heat of vaporization of the water is taken from the hot alkyl polyglycoside film thereby cooling the film and reducing its temperature by about 20° F.–50° F., depending upon the input rate of the injected water. The steam thus formed then counter-currently contacts the remaining portion of the hot alkyl polyglycoside film thereby increasing the efficiency of the alcohol removal by lowering the partial pressure of the alcohol. The lower temperature of the exiting alkyl polyglycoside product results in a product having much more desirable color properties than a similar product produced without the use of water injection in the thin film evaporator. For example, a product exiting at 400° F. typically will have an extinction coefficient in the 10–14 range while a product cooled to 380° F. by water injection will typically have an extinction coefficient in the 6–10 range. The extinction coefficient is determined with a suitable spectrophotometer (e.g. a Spectronic 20) wherein the sample of alkyl polyglycoside is present in an aqueous solution at a concentration of 5% by weight at a path length of 1 cm and at 470 nm wavelength light. The exiting alkyl polyglycoside product also has a higher viscosity because of the cooling effect of the water injection. For example, a product exiting at 400° F. typically will have a viscosity of about 90 centipoise. A product cooled to 380° F. by water injection will typically have a viscosity of about 160 centipoise.

The amount of water fed into the thin film evaporator depends upon the amount of alkyl polyglycoside product introduced into the TFE and can range from about 0.010 pounds of water/pound of alkyl polyglycoside to about 0.035 pounds of water/pound of alkyl polyglycoside. The following examples are meant to illustrate but not to limit the invention.

Example

Procedure for Preparing an Alkyl Polyglycoside Utilizing Water Injection in the TFE A thin film evaporator (TFE) having a surface area of 240 square feet is operated at 430° F. at 3.0 mm Hg. and a film thickness in the range of from 0.1 mm to 10.0 mm at a product loading of 10,000 pounds of crude product per hour which contains 6500 pounds of pure alkyl polyglycoside. Water is injected above the discharge end of the TFE at a rate of from 0.010 to 0.035 lbs of water per pound of pure alkyl polyglycoside.

What is claimed is:

1. A process for the production of an alkyl polyglycoside comprising the steps of (1) reacting a reducing saccharide with excess alcohol to obtain an alkyl polyglycoside reaction product containing unreacted alcohol; (2) forming a thin film by introducing said alkyl polyglycoside reaction product as a liquid into the input end of a thin film evaporation zone having an input end and a discharge end, wherein the pressure inside the thin film evaporation zone is less than about 20 mm Hg and the temperature is from about 300° F. to about 450° F.; (3) contacting the portion of said film nearest to the discharge end of said zone with liquid water thereby converting the water to steam and cooling the portion of the film nearest to said discharge end to reduce its temperature by from about 20° to about 50° F. and (4) contacting the uncooled portion of the film in said zone with said steam to strip the excess alcohol from the alkyl polyglycoside product.

2. The process of claim 1 wherein said sugar is glucose.

3. The process of claim 1 wherein said alcohol is a fatty alcohol having from about 10 to about 18 carbon atoms.

4. The process of claim 1 wherein the amount of water which contacts said film in step (3) is from about 0.010 pounds of water/pound of alkyl polyglycoside to about 0.035 pounds of water/pound of alkyl polyglycoside.

5. The process of claim 1 wherein said alkyl polyglycoside is a compound of the formula I:

$$RO(G)_n \qquad (I)$$

wherein R is a monovalent organic radical containing from about one to about 30 carbon atoms, G is a moiety derived from a reducing saccharide having 5 or 6 carbon atoms and n is a number having an average value from 1 to about 6.

6. The process of claim 5 wherein R is a saturated aliphatic group having from 10 to about 18 carbon atoms.

7. A process for the production of an alkyl polygucoside comprising the steps of (1) reacting glucose with an excess of a fatty alcohol having from about 10 to about 22 carbon atoms to obtain an alkyl polyglucoside reaction product containing unreacted alcohol; (2) forming a thin film by feeding said alkyl polyglucoside as a liquid into the input end of a thin film evaporation zone having an input end and a discharge end, wherein the pressure inside the thin film evaporation zone is less than about 20 mm Hg and the temperature is from about 185° C. to about 210° C.; (3) contacting the portion of said film nearest to the discharge end of said zone with liquid water thereby converting the water to steam and cooling the portion of the film nearest to said discharge end to reduce its temperature by from about 20° to about 50° F.; (4) contacting the uncooled portion of said film in said zone with said steam to strip the excess fatty alcohol from the alkyl polyglucoside product.

8. The process of claim 7 wherein said alcohol is a fatty alcohol having from about 10 to about 18 carbon atoms.

9. The process of claim 7 wherein the amount of water which contacts said film in step (3) is from about 0.010 pounds of water/pound of alkyl polyglycoside to about 0.035 pounds of water/pound of alkyl polyglycoside.

* * * * *